(12) United States Patent
Solanki

(10) Patent No.: US 9,986,896 B2
(45) Date of Patent: Jun. 5, 2018

(54) DISPOSABLE SHEATH DESIGNS FOR THE STIMULATING ENDOSCOPE AND NEEDLE ENDOSCOPES HAVING DISTAL ELECTRODES FOR NERVE BLOCK UNDER DIRECT VISION AND METHODS FOR MAKING AND USING SAME

(75) Inventor: Daneshvari R. Solanki, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1235 days.

(21) Appl. No.: 12/790,938

(22) Filed: May 31, 2010

(65) Prior Publication Data

US 2010/0324363 A1    Dec. 23, 2010

Related U.S. Application Data

(63) Continuation-in-part of application No. 12/398,312, filed on Mar. 5, 2009, now abandoned.

(60) Provisional application No. 61/034,092, filed on Mar. 5, 2008.

(51) Int. Cl.
*A61B 1/00* (2006.01)
*A61N 1/05* (2006.01)
*A61N 1/36* (2006.01)
*A61B 5/00* (2006.01)

(52) U.S. Cl.
CPC ...... *A61B 1/00142* (2013.01); *A61B 1/00087* (2013.01); *A61B 1/00135* (2013.01); *A61N 1/0551* (2013.01); *A61N 1/36021* (2013.01); *A61B 5/4893* (2013.01); *A61N 1/36017* (2013.01)

(58) Field of Classification Search
USPC .......... 600/109, 159, 160, 554, 121; 607/46
See application file for complete search history.

(56) References Cited

U.S. PATENT DOCUMENTS

| | | | |
|---|---|---|---|
| 4,203,430 A | 5/1980 | Takahashi |
| 4,294,233 A | 10/1981 | Takahashi |
| 4,351,323 A | 9/1982 | Ouchi |
| 4,432,349 A | 2/1984 | Oshiro |
| 4,483,326 A | 11/1984 | Yamaka |
| 4,499,895 A | 2/1985 | Takayama |
| 4,557,254 A | 12/1985 | Yamaguchi |
| 4,688,555 A | 8/1987 | Wardle |
| 4,700,693 A | 10/1987 | Lia |
| 4,750,477 A | 6/1988 | Wardle |
| 4,762,118 A | 8/1988 | Lia |
| 4,762,119 A | 8/1988 | Allred, III |
| 4,773,395 A | 9/1988 | Suzuki |
| 4,787,369 A | 11/1988 | Allred, III |
| 4,790,294 A | 12/1988 | Allred, III |
| 4,796,607 A | 1/1989 | Allred, III |

(Continued)

*Primary Examiner* — Timothy J Neal
*Assistant Examiner* — Aaron B Fairchild
(74) *Attorney, Agent, or Firm* — Thomas | Horstemeyer, LLP

(57) ABSTRACT

A nerve blocking endoscope apparatus is disclosed having a disposable sheath and a stimulating assembly including an internal electrode and an external electrode for stimulation of a nerve for identification purposes and to methods for making and using same. A needle nerve blocking endoscope apparatus having an internal electrode for nerve stimulation.

19 Claims, 14 Drawing Sheets

(56) References Cited

U.S. PATENT DOCUMENTS

| | | | | |
|---|---|---|---|---|
| 4,834,069 A | | 5/1989 | Umeda | |
| 4,941,454 A | | 7/1990 | Wood | |
| 4,947,827 A | | 8/1990 | Opie | |
| 4,967,732 A | | 11/1990 | Inoue | |
| 4,996,974 A | | 3/1991 | Ciarlei | |
| 5,005,558 A | | 4/1991 | Aomori | |
| 5,167,221 A | | 12/1992 | Chikama | |
| 5,176,126 A | | 1/1993 | Chikama | |
| 5,259,366 A | * | 11/1993 | Reydel et al. | 600/124 |
| 5,263,928 A | * | 11/1993 | Trauthen et al. | 604/509 |
| 5,299,559 A | | 4/1994 | Bruce | |
| 5,301,656 A | | 4/1994 | Negoro | |
| 5,325,845 A | | 7/1994 | Adair | |
| 5,347,989 A | | 9/1994 | Monroe | |
| 5,359,994 A | | 11/1994 | Kreuter | |
| 5,381,782 A | | 1/1995 | DeLaRama | |
| 5,386,816 A | | 2/1995 | Inoue | |
| 5,389,070 A | * | 2/1995 | Morell | 604/506 |
| 5,396,880 A | | 3/1995 | Kagan | |
| 5,415,158 A | | 5/1995 | Barthel | |
| 5,448,989 A | | 9/1995 | Heckele | |
| 5,464,007 A | | 11/1995 | Krauter | |
| 5,512,035 A | | 4/1996 | Konstorum | |
| 5,531,664 A | | 7/1996 | Adachi | |
| 5,575,755 A | | 11/1996 | Krauter | |
| 5,667,476 A | | 9/1997 | Frassica | |
| 5,681,262 A | * | 10/1997 | Isse | 600/127 |
| 5,681,263 A | | 10/1997 | Flesch | |
| 5,752,912 A | | 5/1998 | Takahashi | |
| 5,830,151 A | * | 11/1998 | Hadzic et al. | 600/554 |
| 5,916,147 A | | 6/1999 | Boury | |
| 5,938,588 A | | 8/1999 | Grabover | |
| 5,960,145 A | | 9/1999 | Sanchez | |
| 6,013,024 A | | 1/2000 | Mitsuda | |
| 6,030,360 A | | 2/2000 | Biggs | |
| 6,203,494 B1 | | 3/2001 | Moriyama | |
| 6,236,876 B1 | | 5/2001 | Gruner | |
| 6,398,776 B1 | | 6/2002 | Sekino | |
| 6,482,148 B1 | | 11/2002 | Luke | |
| 6,491,627 B1 | | 12/2002 | Komi | |
| 6,522,933 B2 | | 2/2003 | Nguyen | |
| 6,585,638 B1 | * | 7/2003 | Yamamoto | 600/114 |
| 6,595,982 B2 | | 7/2003 | Sekino | |
| 6,641,528 B2 | | 11/2003 | Torii | |
| 6,673,060 B1 | | 1/2004 | Fleming | |
| 6,699,183 B1 | | 3/2004 | Wimmer | |
| 6,702,737 B2 | | 3/2004 | Hino | |
| 6,793,622 B2 | | 9/2004 | Konomura | |
| 7,134,993 B2 | | 11/2006 | Lia | |
| 7,150,752 B2 | | 12/2006 | Suzuki | |
| 2007/0287994 A1 | * | 12/2007 | Patel | 606/41 |

\* cited by examiner

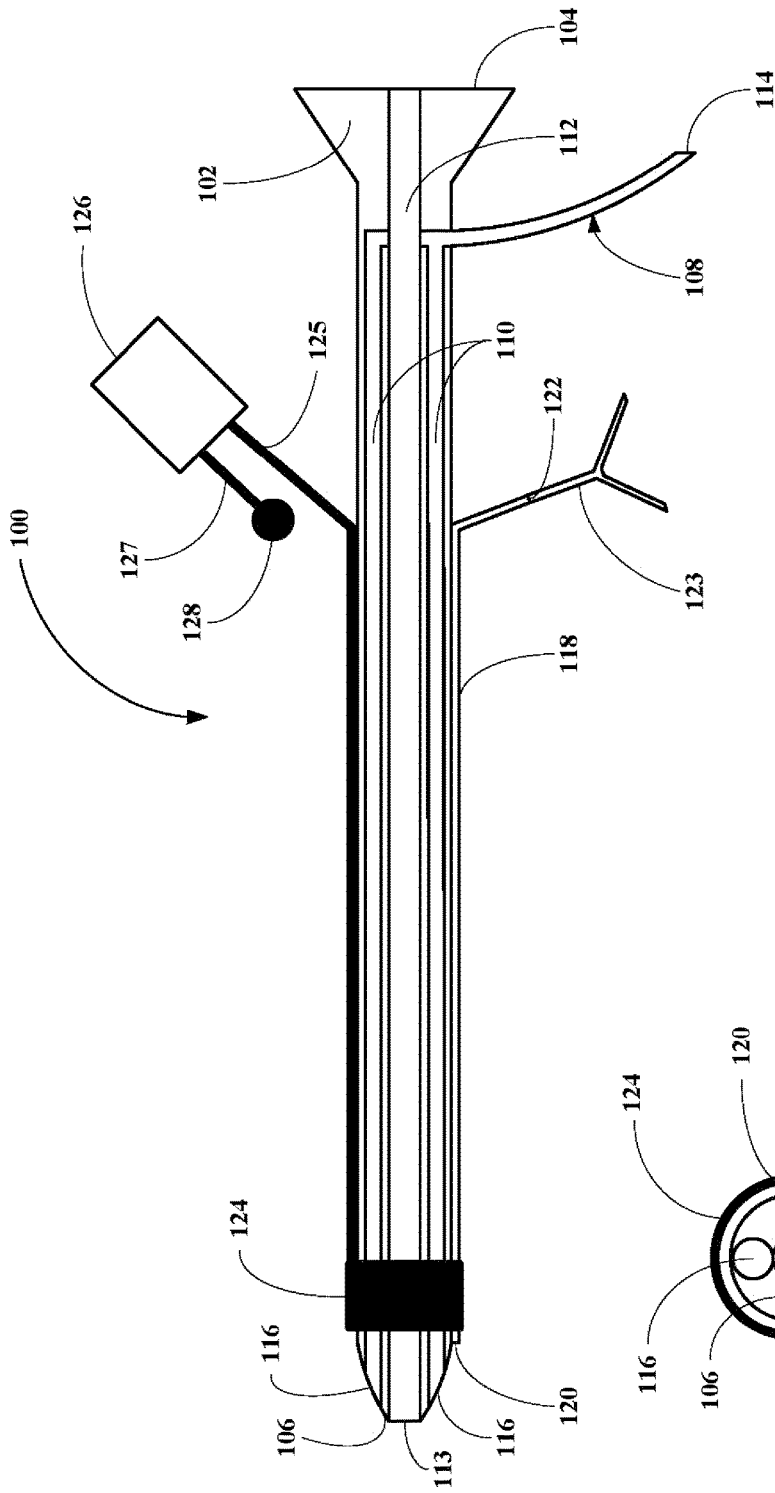
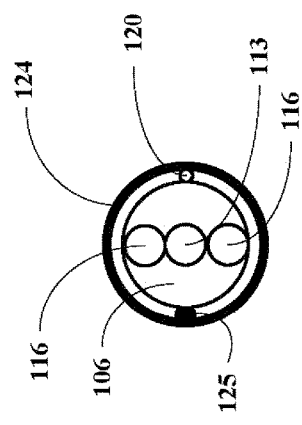
FIG. 1A
FIG. 1B

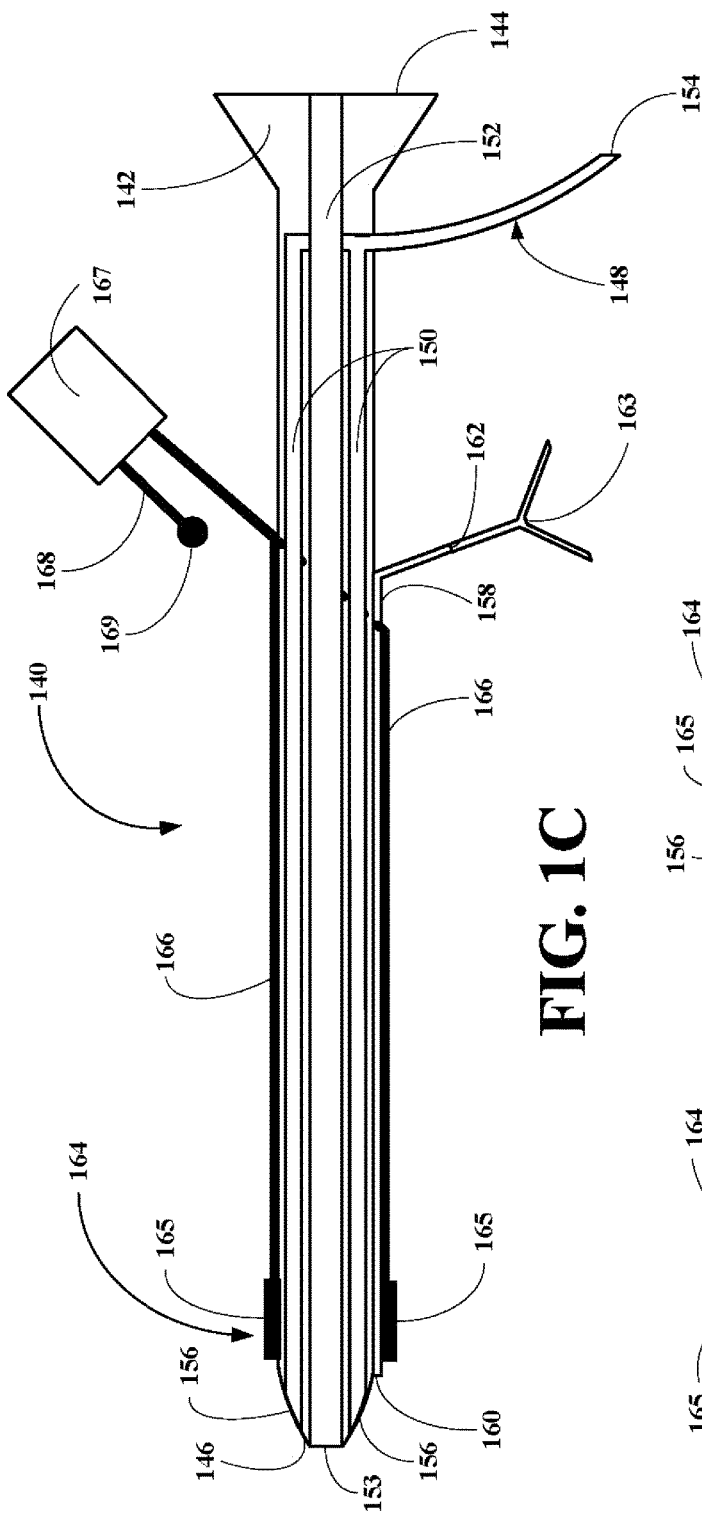

Single Fiber Endoscope with a Stimulating Electrode for Peripheral Nerve Block under Direct Vision

DISPOSABLE SHEATH DESIGNS FOR THE STIMULATING ENDOSCOPE AND NEEDLE ENDOSCOPES HAVING DISTAL ELECTRODES FOR NERVE BLOCK UNDER DIRECT VISION AND METHODS FOR MAKING AND USING SAME

RELATED APPLICATIONS

The present application is a Continuation-in-Part of U.S. patent application Ser. No. 12/398,312, filed 5 Mar. 2009, which claims the benefit and priority to U.S. Provisional Patent Application Ser. No. 61/034,092 filed 5 Mar. 2008.

BACKGROUND OF THE INVENTION

1. Field of the Invention

Embodiments of the present invention relate to an endoscope for peripheral nerve blocks under direct observational control via the endoscope and to methods for making and using same. The new embodiments of the present invention relate to endoscope sheaths for use with endoscopes used in peripheral nerve blocks.

More particularly, embodiments of the present invention relate to an endoscope including a stimulating electrode disposed at its distal end. Such an endoscope, when properly positioned under direct observational control via the endoscope, permits effective endoscope placement and electrode stimulation of the nerve for achieving effective peripheral nerve blocks under direct control using a local anesthetic agent. The new embodiments of the present invention also relate to endoscope sheaths including a stimulating electrode. The present invention also relates to methods for making and using same.

2. Description of the Related Art

The technology of video assisted procedures using endoscopy is available and is not new. Video assisted endoscopic procedures are used for vein harvesting, thyroid surgery, carpel tunnel release, etc. But all these techniques require a surgical incision.

Presently the peripheral nerve blocks are done using indirect methods like paresthesias, peripheral nerve stimulation and ultrasound guided techniques.

However, there are no video assisted endoscopic procedures available at present for the performance of peripheral nerve blocks for regional anesthesia including a stimulating electrode. Thus, there is a need in the art that is satisfied by this invention, where the present invention provides an apparatus and method for performing video assisted endoscopic peripheral nerve blocks for regional anesthesia under direct vision or through the use of a video monitor to permit electrode stimulation of a nerve, to insure proper identification of the nerve to be blocked via electrical stimulation. The present invention also provides sheaths adapted to surround a traditional endoscope and to permit electrode stimulation of a nerve, to insure proper identification of the nerve to be blocked via electrical stimulation.

SUMMARY OF THE INVENTION

Original Embodiments

Embodiments of the present invention provide an endoscope including a stimulating electrode disposed at its distal end, where the endoscope, when properly positioned under direct observational control via the endoscope via the introducer, permits effective electrode placement adjacent to a nerve to be simulated for achieving effective peripheral nerve blocks. The endoscope may also include a fluid injection conduit having an opening at or near the distal end of the endoscope.

Embodiments of the present invention provide a method for performing a nerve block of a peripheral nerve including the steps of introducing an endoscope percutaneously without a surgical incision into an animal including a human. The endoscope includes an electrode disposed at or near its distal end and connected to a stimulation unit via a conducting conduit or wire. Once the endoscope has been inserted, the endoscope is pushed into a tissue of an animal including a human under direct visual control or visual control using a video monitor until the electrode is adjacent a peripheral nerve to be blocked. After the electrode is properly positioned, the nerve can be blocked using a local anesthetic injection through a fluid conduit to produce anesthesia so that a surgical procedure can then be performed. The conduit for administering anesthesia can also be used to place a stimulating catheter or a non-stimulating catheter to be left in place so that additional amounts of the anesthetic agents can be administered to the nerve to maintain the block or provide postoperative pain control. The endoscope can then be removed.

Embodiments of the present invention provide an endoscopic apparatus for locating peripheral nerve blocks including a body having a proximal end and a distal end. The apparatus also includes a light delivery assembly having one light delivery conduit or a plurality of light delivery conduits and one light receiving conduit or a plurality of light receiving conduits, where each light delivery conduit is connected to a light source and terminates in the distal end of the body, and where each light receiving conduit is connected to an image processing and terminates in the distal end of the body. The apparatus also includes a fluid delivery assembly including a fluid conduit terminating in an exit port near a distal end of the body and connected to fluid delivery unit adapted to deliver fluid through the fluid conduit. The apparatus also includes a nerve stimulating assembly including a nerve simulator unit having a first electrode disposed at or near the distal end of the body and connected via a first conducting conduit to the nerve stimulator unit, and a second electrode adapted to be placed on the skin of a patient and connected via a second conducting conduit to the nerve stimulator unit to produce a voltage between the first and second electrodes, where the voltage stimulates a nerve response when the first electrode is proximal a nerve. The distal end of the body is adapted to be inserted into an animal including a human, where the progress of the insertion is monitored by the image processing and display unit so that the distal end can be properly situated adjacent a nerve to be blocked and where the nerve simulator is adapted to properly identify the nerve to be blocked and where the fluid delivery assembly is adapted to deliver a nerve blocking agent to the identified nerve. In certain embodiments, the first electrode surrounds a portion of the body near its distal end. In other embodiments, the first electrode comprises a ring. In other embodiments, the ring is a solid ring, metal foil ring, or a wire mesh ring. In other embodiments the first electrode comprises at least one electrode element. In other embodiments, the first electrode comprises a plurality of electrode element. In other embodiments the first electrode comprises a plurality of electrode element equal spaced around an outside surface of the body near the distal end of the body. In other embodiments, the apparatus further includes a catheter adapted to be fed through the fluid conduit and left in place after removal of the endoscope. In other embodiments, the fluid delivery assembly includes a Y-connector so that the type of fluid introduced into the fluid conduit can be changed. In still other embodiments, the light delivery and receiving conduits comprises optical fibers or optical fiber bundles.

Embodiments of the present invention also provide a method for blocking a nerve including the step of inserting an endoscopic apparatus of this invention into a tissue site of an animal including a human. The method also includes the step of guiding the distal end of the apparatus by viewing progress of the insertion on the image processing and display unit. The method also includes the step of positioning the distal end of the endoscope adjacent to a peripheral nerve to be blocked. The method also includes the step stimulating the nerve with the stimulating electrode to identify the nerve and to ensure proper placement of the distal end of the apparatus. In certain embodiment, the method further includes the step administering a local anesthetic agent into the tissue site to block the identified nerve to produce anesthesia in the nerve so a surgical procedure can be subsequently performed. In other embodiments, the method further includes the step of inserting a catheter into the site through the fluid conduit and removing the apparatus so that the nerve can be blocked for a period of time after surgery.

New Embodiments

Embodiments of the present invention provide an endoscope apparatus including: (1) an endoscope sheath having an opened distal end and an opened proximal end, and (2) an electronic unit including a first terminal, a first lead, an endoscope attachment member, a second terminal, a second lead and a skin patch including a second electrode, where the apparatus is adapted to receive an endoscope, where the endoscope attachment member is adapted to be connected to a proximal end of an endoscope so that a distal end of the endoscope which extends out past the sheath acts as a first electrode completely a circuit and permitting electrical nerve stimulation.

Embodiments of the present invention provide an endoscope apparatus including: (1) an endoscope sheath having a closed distal end including a transparent window and an opened proximal end and (2) an electronic unit including a first terminal, a first lead, a first electrode disposed near the closed distal end of the sheath, a second terminal, a second lead and a skin patch including a second electrode, where the skin patch completes a circuit and permitting nerve block, once placed on the skin above the first electrode.

Embodiments of the present invention provide methods for performing a nerve block of a peripheral nerve including inserting an endoscope apparatus percutaneously into an animal including a human, where the endoscope apparatus includes an endoscope, an endoscope sheath apparatus surrounding the endoscope and a nerve stimulating assembly. The apparatus includes a first electrode disposed at or near a distal end of the endoscope apparatus to be located adjacent a nerve to be blocked and a skin patch including a second electrode to be situated above the distal end of the endoscope apparatus. Once the endoscope apparatus has been inserted, the apparatus is pushed into a tissue of an animal including a human under direct visual control or visual control using a video monitor until the first electrode is adjacent a peripheral nerve to be blocked. The apparatus also includes a conduit for administering local anesthetic agents, a catheter, other agents or object to a peripheral nerve site. After the electrodes are properly positioned, the nerve can be stimulated to insure that a correct nerve will be blocked. Once the nerve has been confirmed, a local anesthetic agent is injected through the conduit to produce anesthesia so that a surgical procedure can then be performed. The conduit for administering anesthesia can also be used to place a stimulating catheter or a non-stimulating catheter to be left in place so that additional amounts of the anesthetic agents can be administered to the nerve to maintain the block or provide agents for postoperative pain control. The endoscope apparatus can then be removed.

Embodiments of the present invention provide an endoscope apparatus including an endoscope, an endoscope sheath apparatus surrounding the endoscope and a nerve stimulating assembly. The apparatus also includes a light delivery assembly having one light delivery conduit or a plurality of light delivery conduits and one light receiving conduit or a plurality of light receiving conduits. Each light delivery conduit is connected to a light source and terminates in the distal end of endoscope. Each light receiving conduit is connected to an image processing unit and terminates in the distal end of the endoscope. The apparatus also includes a conduit terminating in an exit port near a distal end of the endoscope apparatus. If the conduit is used as a fluid conduit, then a proximal end of the conduit is connected to a fluid delivery unit adapted to deliver fluid through the conduit. The nerve stimulating assembly including a nerve stimulating unit, a first electrode and a second electrode. The first electrode is disposed at or near the distal end of the endoscope apparatus, where the first electrode is connected to the nerve stimulating unit via a first conducting conduit or a first lead. The second electrode is adapted to be placed on the skin of a patient and connected to the nerve stimulating unit via a second conducting conduit or second lead to produce a voltage across the electrodes, where the voltage produces a current that stimulates a nerve response when the first electrode is proximal a nerve. The distal end of the endoscope apparatus is adapted to be inserted into an animal including a human, where the progress of the insertion is monitored by direct viewing or by image processing of the images on a display unit so that the distal end and the first electrode can be properly situated adjacent a nerve to be blocked and where the nerve stimulating assembly is adapted to properly identify the nerve to be blocked and where the fluid delivery assembly is adapted to deliver a nerve blocking agent to the identified nerve. In certain embodiments, the first electrode is the distal end of the endoscope. In other embodiments, the first electrode is disposed near a distal end of the endoscope sheath apparatus, where the electrodes can be a ring or one or a plurality of separate electrode elements distributed symmetrically or otherwise about or in the sheath. The ring can be a solid ring, a metal foil ring, or a wire mesh ring. In other embodiments, the first electrode comprises at least one electrode element. In other embodiments, the first electrode comprises a plurality of electrode element equal spaced around or in the endoscope sheath apparatus near its distal end. In other embodiments, the apparatus further includes a catheter adapted to be fed through the conduit and left in place after removal of the endoscope apparatus. In other embodiments, the fluid delivery assembly includes a Y-connector so that the type of fluid introduced into the conduit can be changed. In still other embodiments, the light delivery and receiving conduits comprises optical fibers or optical fiber bundles.

Embodiments of the present invention also provide a method for blocking a nerve including the step of inserting an endoscopic apparatus of this invention into a tissue site of an animal including a human. The method also includes the step of guiding the distal end of the apparatus by viewing progress of the insertion directly or on the image processing and display unit. The method also includes the step of positioning the distal end of the endoscope apparatus adjacent to a peripheral nerve to be blocked. The method also includes the step stimulating the nerve using the stimulating electrodes to identify the nerve and to ensure proper placement of the distal end of the apparatus. In certain embodiment, the method further includes the step administering a local anesthetic agent into the tissue site to block the identified nerve to produce anesthesia in the nerve so a surgical procedure can be subsequently performed. In other embodiments, the method further includes the step of inserting a catheter into the site through the conduit and removing the apparatus so that the nerve can be blocked prior to surgery, during surgery and/or for a period of time after surgery.

Needle Endoscopes

Embodiments of this invention also related to needle endoscopes having an electrode disposed at or near their distal ends. Very fine endoscopes having high resolution are available. They are used in the automotive and airline industries. The smallest endoscopes available have diameters between about 0.5 mm and about 1 mm. The medical field generally uses 16 gauge to 18 gauge needles. The present invention provides a needle endoscope having a diameter between about 16-gauge and about 18-gauge needles. In other embodiments, the needle endoscopes have a diameter between about 0.5 mm and about 1 mm. The needle endoscope includes a stimulating electrode disposed at or near its distal end. The electrode has a conduit for injecting a local anesthetic solution. When this electrode is placed in the proximity of a nerve and the nerve is stimulated, the local anesthetic may be injected next to the nerve through the electrode to block that particular nerve. The needle endoscope may also have a conduit in the needle itself. This method of using needle endoscope may eliminate 2-3 steps and we will still be able to do the nerve block under direct vision as described before.

Embodiments of this invention also related to methods for using needle endoscopes having an electrode disposed at or near their distal ends. The methods include inserting the endoscope into a tissue site adjacent a near to be blocked. The methods then include stimulating a nerve to insure that the nerve is the correct nerve to be blocked. The methods then include injecting a local anesthetic agent into the tissue site to block the nerve.

In all of these embodiments, the first electrode is an internal electrode, which is positioned adjacent a nerve for stimulation confirmation prior to administering a nerve blocking agent and the second electrode is an external electrode, which is position on the skin of an animal including a human so that a voltage can be applied across the electrodes to produce a stimulating current.

BRIEF DESCRIPTION OF THE DRAWINGS

The invention can be better understood with reference to the following detailed description together with the appended illustrative drawings in which like elements are numbered the same.

Original Figures

FIGS. 1A-B depict an embodiment of an endoscope of this invention including a ring type stimulating electrode disposed at or near a distal end of the endoscope.

FIGS. 1C-E depict another embodiment of an endoscope of this invention including a stimulating electrode comprising a set of electrode ends disposed at or near a distal end of the endoscope.

New Figures

Figure 7A:
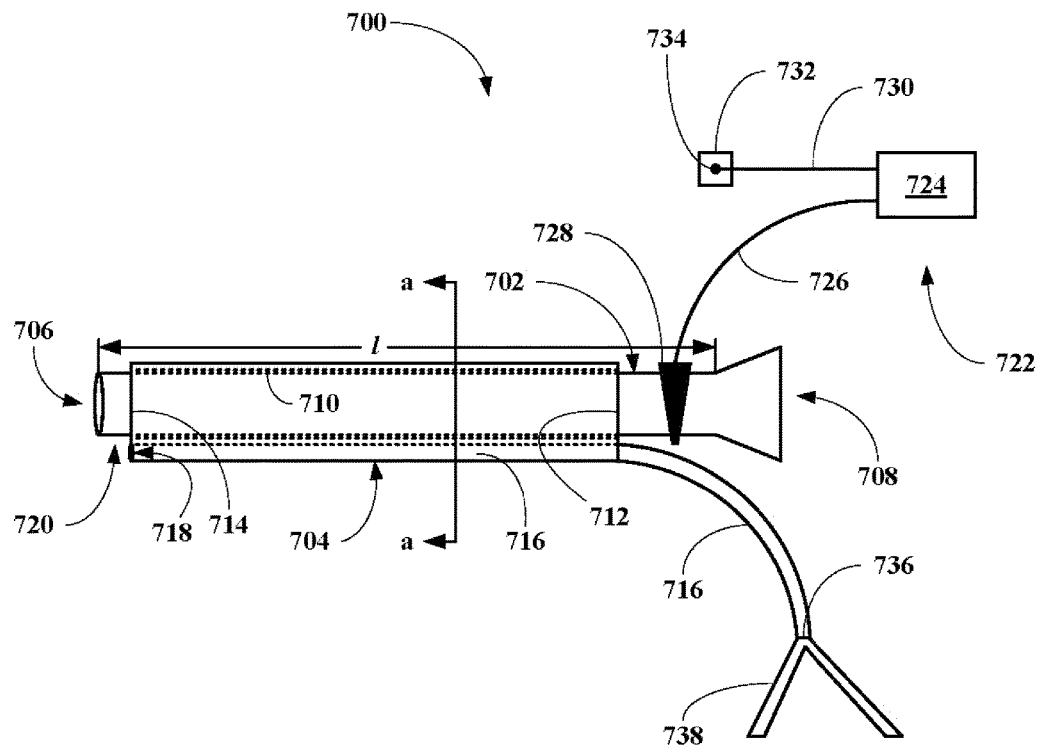
Figure 7B:
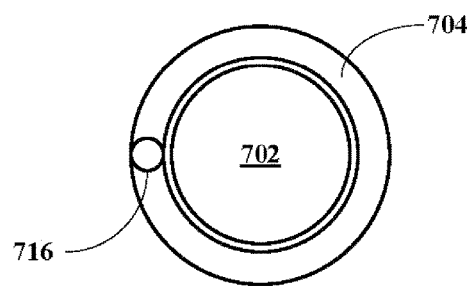

FIGS. 7A&B depict an embodiment of an endoscope sheath apparatus of this invention including a stimulating assembly and a sheath having an opened distal, an opened proximal end and a conduit.

Figure 8A:
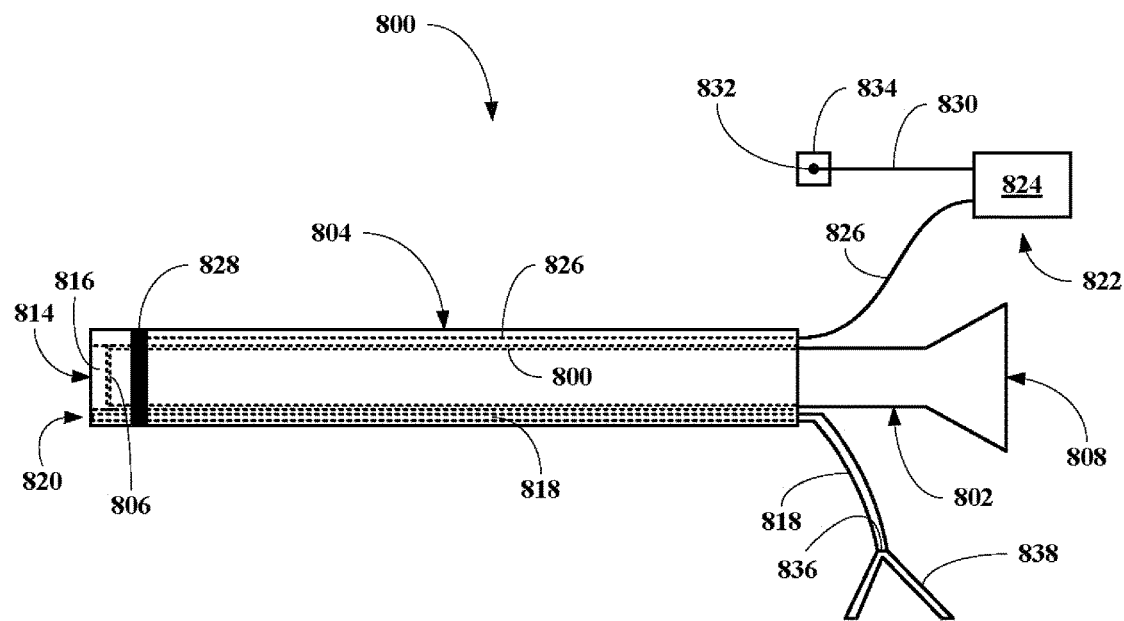
Figure 8B:
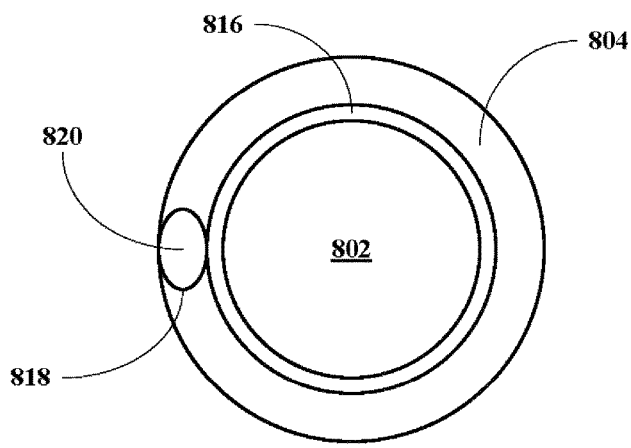

FIGS. 8A&B depict another embodiment of an endoscope sheath apparatus of this invention including a stimulating assembly and sheath having a closed distal end including a transparent window and an opened end.

Needle Endoscopes

Figure 9A:
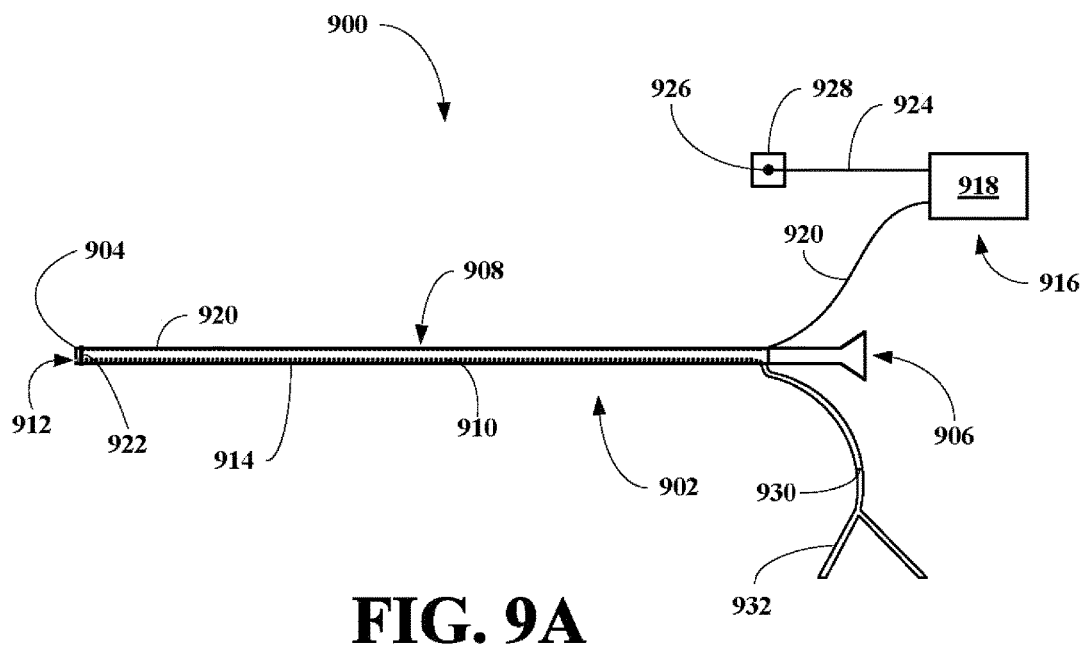

FIGS. 9A&B depict an embodiment of a needle endoscope apparatus of this invention including a stimulating assembly.

DETAILED DESCRIPTION OF THE INVENTION

The inventor has found that a new endoscope apparatus can be constructed with a distally disposed electrode for performing safe, efficient and effective peripheral nerve blocking. The apparatus is designed to be inserted percutaneously into a tissue of an animal including a human as a conventional endoscope. The distal end is then positioned so that the electrode is located adjacent to a nerve to be blocked to perform a nerve block. The electrode is then activated to stimulate the nerve and ensure proper placement of endoscope adjacent the nerve so that anesthesia administration can be performed safely, efficiently and effectively for the surgical procedure. This process is performed without the need for a surgical incision unlike other endoscopic procedures.

The present invention broadly relates to an endoscope apparatus including a rigid or flexible body, a light source and a light conduit for transmitting light from the light source to a distal end of the body of the endoscope. The endoscope apparatus also includes a light receiving conduit having its proximal end disposed in or at the distal end of the endoscope body and its distal end in optical communication with a monitor for observing a location of the distal end of the endoscope body as it is positioned into a tissue of an animal including a human adjacent a peripheral nerve to be blocked, where proper endoscope positioning is confirmed by nerve stimulation via an electrode disposed at or near a distal end of the endoscope. The electrode is connected via a conducting conduit or wire and to an electrode stimulating unit, where the unit also includes a second conducting conduit or wire leading to a skin contact pad which acts as ground.

The present invention broadly relates to a method for blocking a nerve including the step of inserting an endoscope apparatus of this invention into a tissue of an animal including a human and positioning the distal end of the endoscope adjacent to a peripheral nerve to be blocked. The electrode disposed on or at the distal end is then turned on to stimulate of the nerve to ensure proper endoscope placement under direct visual or video assisted visual control. Once proper endoscope placement is confirmed, a local anesthetic agent is then injected into the tissue site to block the appropriate nerve to produce anesthesia in its distribution of the nerve so a surgical procedure can be subsequently performed. The local anesthetic administering like a catheter can be left in place so that the nerve can be blocked for a period of time after surgery. The endoscope can then be removed.

The present invention having the following general aspects that make it uniquely suited for performing nerve blocking: (1) the endoscope has a length between about 5" and about 10"; (2) the endoscope can be rigid or flexible; (3) the endoscope can be a fiberoscope or fiberoscope fiber; (4) the endoscope is adapted to be easy to maneuver so that it can be positioned efficiently and effectively adjacent a location on a peripheral nerve; (5) the endoscope is adapted to have an excellent optical resolution; (6) the endoscope is adapted to be introduced percutaneously through a trocar or an introducer; (7) no surgical incision is needed to introduce the endoscope; (8) the trocar can optionally include a regulated side port for introduction of dilating medium for distension of the tissues if needed; (9) the trocar can optionally have a second port. This port can be used for introduction of the stimulating needle or placement of perineural catheter, placement of stimulating catheter. So, the nerve can be stimulated under direct vision or the catheter can be threaded under direct vision minimizing the chances of trauma to the nerves and the blood vessels; (10) the trocar is adapted to have capability for placing a deflated balloon and such a balloon when inflated can provide distension of the tissues so the nerves and the blood vessels can be easily visualized; (11) the endoscope also includes a anesthesia port for administering an anesthetic agent after proper placement of the endoscope; and (12) the endoscope includes a side port with a distal opening that can be used to inject the local anesthetic and placing a perineural catheter The endoscope of this invention combines direct vision and a stimulating electrode like the stimulating needle to improve the efficacy of performing peripheral nerve blocks. In certain embodiment, the endoscope will have a bullet tip so it is atruamatic. The endoscope is adapted to permit visualization for proper electrode placement and stimulation under direct vision of the distally disposed electrode of the endoscope. With an appropriate response the nerve can be anesthetized by injection of a minimum amount of a local anesthetic under direct vision to produce the nerve block.

The endoscopes of this invention will also have other applications including, without limitation: (1) perineural catheter placement to reduce failed blocks and to permit pain control; (2) blood vessels will be visible, especially central veins. These can be cannulated under direct vision and help prevent complications like arterial punctures and pneumothorax etc. It can help in doing some interventional pain procedures under direct vision and help minimize exposure to X-ray radiation as these presently are done under fluoroscopic guidance (Endoscopes can also be used for surgery performed under the skin or muscles as well as the repair of the peripheral nerves); (3) the endoscopes can include distension of tissues using gas like carbon dioxide at low pressures of about 1 to about 8 mm Hg or other fluid. The tissue distension can also be accomplished using a balloon.

The peripheral nerve blocks at present are mostly done by placing percutaneous stimulating needles percutaneously based on the anatomic knowledge of the location of the nerves. Some institutions now use ultrasound guidance for performing peripheral nerve blocks. This requires the use of ultrasound gel and lack of it or improper contact with it makes it hard to visualize the nerves. So direct vision would be a great advantage and would greatly facilitate efficient and effective nerve blocking. Although endoscopes are available, none have been used for this technique. The endoscope having a stimulating electrode will allow us to locate the nerve, stimulate the nerve and anesthetize the nerve all under direct visual control. Such a method will also allow us to deal with variations in anatomy. Some times rescue blocks are necessary to have complete anesthesia. This endoscopic method will allow the anesthesiologist to perform such rescue blocks expeditiously. On an average at University of Texas Medical Branch in Galveston, TS, we perform between 50 and 100 peripheral nerve blocks for regional anesthesia per month. We perform between 80 and 100 pain blocks per month and more than 40-60 ventral vein cannulations per month.

Anesthesiologists do the peripheral blocks and place central venous lines. Interventional pain physicians perform interventional pain procedures under fluoroscopic guidance. Anesthesiologists, internists, surgeons and critical care physicians place the central venous catheters. Versatility of the endoscope and user friendly features will allow for accurate placement of the stimulating catheter or needle for vascular puncture.

Nerve blocks are performed for surgical anesthesia and postoperative analgesia. The endoscopic method with a stimulating electrode will allow one to localize the nerve under direct visual control and anaesthetize the chosen nerve. This can improve the accuracy of placement of the nerve block and decrease the chances of nerve damage. It will also decrease the time it takes to do the nerve block. The volume of local anesthetic required to produce anesthesia or analgesia of that nerve will be much less as it is placed directly on the target and this also decreases the chances of producing local anesthetic toxicity. In certain embodiments, the endoscope will have a bullet tip so it minimizes the chances of causing damage to the nerves and prevents the inadvertent puncture of a blood vessel, which could lead to systemic toxicity to other organs in the body.

New Disclosure

More recently, the inventor has found that disposable sheaths can be constructed to accomplish the goal of providing endoscopes with nerve stimulating capabilities. These sheath apparatuses are practical and economical to manufacture.

First Sheath Embodiment

The first embodiment provides a sheath apparatus of this invention includes a sheath adapted to be mounted on a stem of an endoscope. The sheath is adapted to fit over the stem of the endoscope and cover at least 50% of the length of the stem of the endoscope. In certain embodiments, the sheath is adapted to fit snugly onto the stem of the endoscope and cover the stem of the endoscope except for a length at its distal end so that a portion of the endoscope extends past the sheath. In other embodiments, the sheath extends from a distal location to a proximal location of the stem of the endoscope. In other embodiments, the distal location is about 5 mm from the distal end of the stem and the proximal location is about 10 mm of the proximal end of the stem of the endoscope. The sheath apparatus includes a conduit extending from the distal end of the sheath and extending out from the proximal end of the sheath. The conduit can be used to insufflate a dilating agent like carbon dioxide into the tissue of the animal to assist insertion of the endoscope apparatus. The conduit can also be used to inject a local anesthetic agent into the tissue adjacent a nerve, identified by electrode stimulation, to produce a nerve block. Once the sheath is placed on the endoscope a metal alligator clip or other attachment member can be detachably connected to a proximal end of the endoscope near a viewing eye piece. The clip or member is then connected to the nerve stimulating assembly. Once the skin electrode is placed on the animal above the distal end of the endoscope, the two electrodes are attached to the stimulating assembly and a voltage is applied across the electrodes causing a current to flow through the stem. The current travels down the stem, but does not affect the tissue in contact with the stem portion as the tissue is isolated by the sheath. The exposed distal tip of the stem of the endoscope apparatus acts as the internal or first electrode. The current can then be used to stimulate a nerve. The sheath is disposable and after a single use can be discarded. The endoscope will still need to be sterilized before the next use. Another embodiment described below can potentially eliminate the need to sterilize the endoscope between use.

Second Sheath Embodiment

The stimulating endoscope needs to be sterilized after each use. This can limit its use in patients with diseases like hepatitis C and HIV. To circumvent that problem, a second embodiment of a disposable sheath can be constructed that can be mounted directly on the endoscope so that it can be discarded after a single use, without risking contamination of the endoscope. The sheath apparatus includes a closed end having a central transparent membrane or window adapted to permit endoscope light to shine therethrough so that the endoscope can be directly guided. The sheath apparatus also includes a conduit having an exit port near its distal end that can be utilized to insufflate a dilating agent such as carbon dioxide. The conduit can be used to inject local anesthetic directly on a nerve to be blocked. The same conduit can also be used to place a catheter for continuous infusion for postoperative analgesia. The proximal end of the sheath includes a locking device so that once the endoscope is inserted into the sheath, the endoscope is held secure and will not dislodge during insertion and used. The sheath apparatus also includes an electrode on its outer surface disposed near the distal end of the apparatus, where the electrode is used to stimulate a nerve using a current such as a 2 mA current. The electrode is connected to the stimulating assembly via a wire. The wire can be fused to the inner surface of the sheath or formed in the sheath. The electrode can be formed on the outer surface of sheath or inlet into the sheath. The sheath apparatus can be discarded after a single use.

Original Endoscopes of this Invention

Referring now to FIGS. 1A&B, an embodiment of an apparatus of this invention, generally 100, is shown to include a body 102 having a proximal end 104 and a distal end 106. The apparatus 100 also includes a light delivery assembly 108 having two light delivery conduits 110 and a light receiving conduit 112, where the light delivery assembly 108 is connected to a light source (not shown) at its proximal end 114 and where the conduits 110 terminate in the distal end 106 of the body 102. Light exiting distal ends 116 of the conduits 110 are used to illuminate tissue as the endoscope 100 is inserted into a site of an animal including a human and a portion of the reflected light is received by a distal end 113 of the receiving conduit 112, where it can be directly viewed and/or travels to an image processing and display unit not shown. The apparatus 100 also includes a fluid conduit 118 terminating in an exit port 120 near a distal end 106 of the body 102. A proximal end 122 of the fluid conduit 118 is optionally fitted with a Y-connector 123 so that the type of fluid introduced into the fluid conduit 118 can be changed or a fluid, especially a gas, can be introduced to dilate the tissue so that the tissue can be visualized easily. The apparatus 100 also includes a ring shaped stimulating electrode 124 connected via a conducting conduit 125 to a nerve stimulator 126 having a second conducting conduit 127 including a second electrode 128 adapted to be placed on the skin to act as ground and to produce a voltage at the ring electrode 124. The electrode 124 can be composed of any conductor and can be of any size. In certain embodiments, the electrode 124 is a thin metal foil. Generally, the light delivery and receiving conduits comprises one or a plurality of optical fibers or optical fiber bundles. In certain embodiment, the light delivery and receiving conduits are a single fiber or microfiber.

For further details on the type of endoscopes that can be equipped with an electrode new block stimulator of this invention include at least the endoscopes disclosed in U.S. Pat. Nos. 7,150,752, 7,134,993, 6,793,622, 6,702,737, 6,699,183, 6,673,060, 6,641,528, 6,595,982, 6,522,933, 6,491,627, 6,482,148, 6,398,776, 6,236,876, 6,203,494, 6,030,360, 6,013,024, 5,960,145, 5,938,588, 5,916,147, 5,752,912, 5,681,263, 5,667,476, 5,575,755, 5,531,664, 5,512,035, 5,464,007, 5,448,989, 5,415,158, 5,396,880, 5,386,816, 5,381,782, 5,359,994, 5,347,989, 5,325,845, 5,301,656, 5,299,559, 5,176,126, 5,167,221, 5,005,558, 4,996,974, 4,967,732, 4,947,827, 4,941,454, 4,834,069, 4,796,607, 4,790,294, 4,787,369, 4,773,395, 4,762,119, 4,762,118, 4,750,477, 4,700,693, 4,688,555, 4,557,254, 4,499,895, 4,483,326, 4,432,349, 4,351,323, 4,294,233, and 4,203,430, incorporated herein by reference.

Referring now to FIGS. 1C-E, an embodiment of an apparatus of this invention, generally 140, is shown to include a body 142 having a proximal end 144 and a distal end 146. The apparatus 140 also includes a light delivery assembly 148 having two light delivery conduits 150 and a light receiving conduit 152, where the light delivery assembly 148 is connected to a light source (not shown) at its proximal end 154 and where the conduits 150 terminate in the distal end 146 of the body 142. Light exiting distal ends 156 of the conduits 150 is used to illuminate tissue as the endoscope is inserted into a site of an animal including a human and a portion of the reflected light is received by a distal end 153 the receiving conduit 152, where it travels to an image processing and display unit not shown. The apparatus 140 also includes a fluid conduit 158 terminating in a exit port 160 near a distal end 146 of the body 142. A proximal end 162 of the fluid conduit 158 is fitted with a Y-connector 163 so that the type of fluid introduced into the fluid conduit 158 can be changed or to use the fluid conduit to inject a component such as a gas to dilate the tissue. The apparatus 140 also includes a two element stimulating electrode 164 having two elements 165 connected via conducting conduits 166 to a nerve stimulator 167 having a second conducting conduit 168 including a second electrode 169 adapted to be placed on the skin to produce a voltage at the ring electrode 164 as shown in FIG. 1D. Looking at FIG. 1E, a second element stimulating electrode 164 is shown having four stimulating elements 165.

Figure 1F:
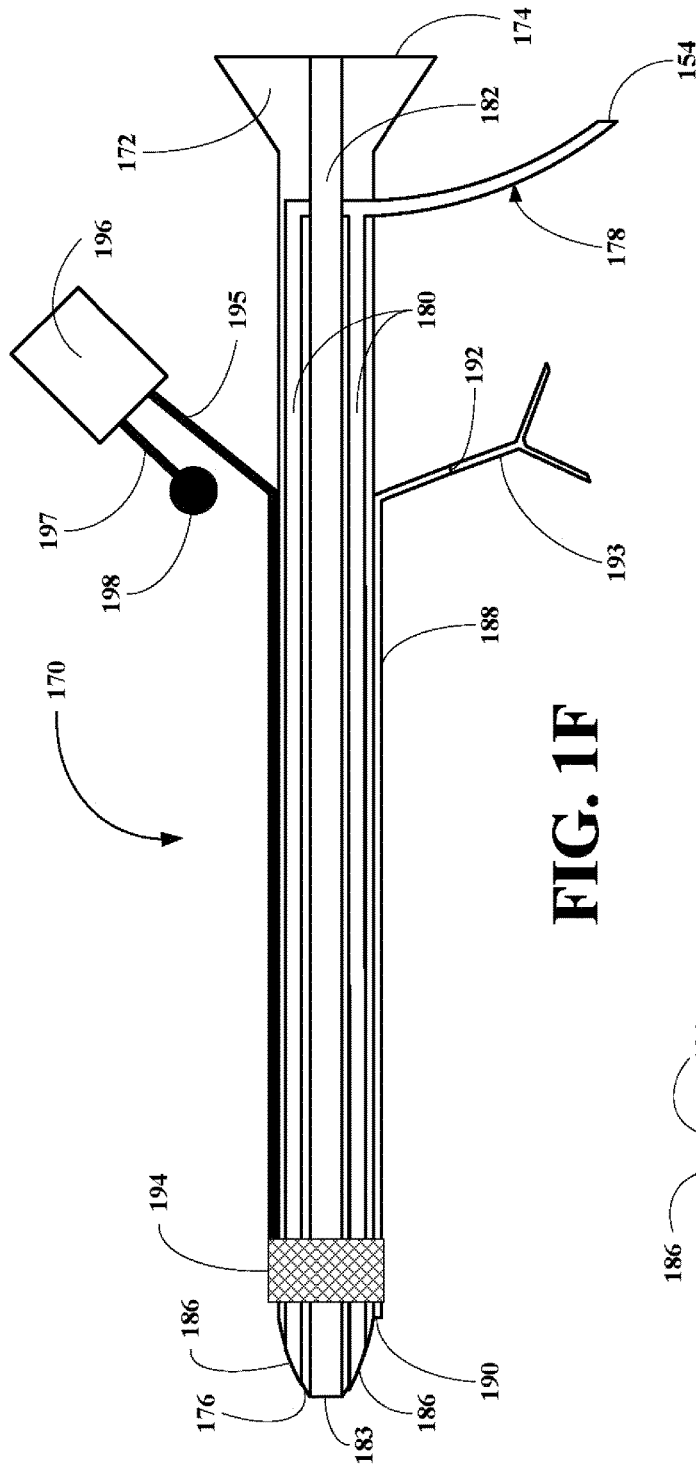
FIGS. 1F-G depict another embodiment of an endoscope of this invention including a mesh type stimulating electrode disposed at or near a distal end of the endoscope.
Figure 1G:
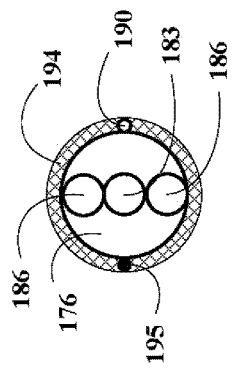

Referring now to FIGS. 1F&G, an embodiment of an apparatus of this invention, generally 170, is shown to include a body 172 having a proximal end 174 and a distal end 176. The apparatus 170 also includes a light delivery assembly 178 having two light delivery conduits 180 and a light receiving conduit 182, where the light delivery assembly 178 is connected to a light source (not shown) at its proximal end 184 and where the delivery conduits 180 terminate in the distal end 176 of the body 172. Light exiting distal ends 186 of the conduits 180 is used to illuminate tissue as the endoscope is inserted into a site of an animal including a human and a portion of the reflected light is received by a distal end 183 the receiving conduit 182, where it travels to an image processing and display unit not shown. The apparatus 170 also includes a fluid conduit 188 terminating in a exit port 190 near a distal end 176 of the body 172. A proximal end 192 of the fluid conduit 188 is fitted with a Y-connector 193 so that the type of fluid introduced into the fluid conduit 188 can be changed or to use the fluid conduit to withdraw fluids from the site. The apparatus 100 also includes a ring shaped mesh stimulating electrode 194 connected via a conducting conduit 195 to a nerve stimulator 196 having a second conducting conduit 197 including a second electrode 198 adapted to be placed on the skin to produce a voltage at the mesh electrode 194.

Figure 2A:
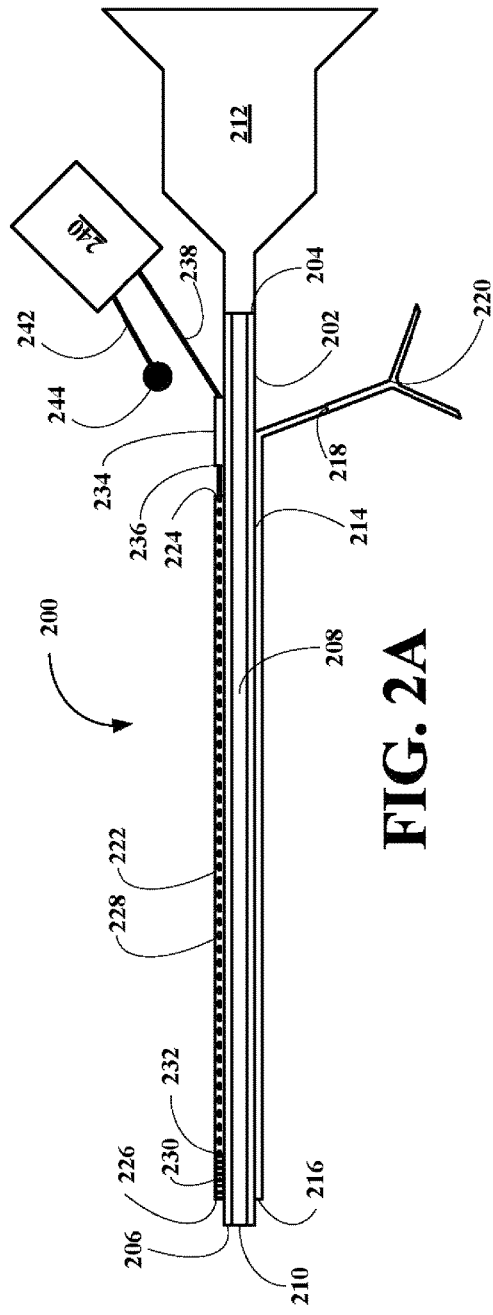
FIGS. 2A-C depict another embodiment of an endoscope of this invention including a retractable type stimulating electrode disposed at or near a distal end of the endoscope.
Figure 2C:
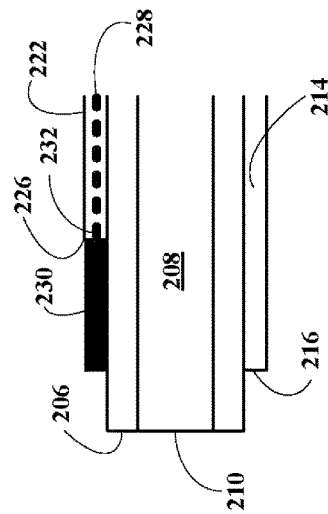
Figure 2B:
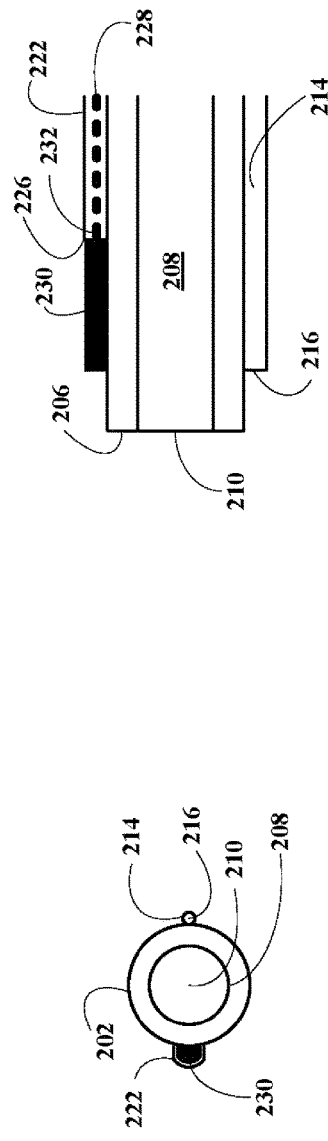

Referring now to FIGS. 2A-C, an embodiment of an apparatus of this invention, generally 200, is shown to include a body 202 having a proximal end 204 and a distal end 206. The apparatus 200 also includes a single optical fiber 208 adapted to deliver incident light to and receive reflected light from a tissue site into which the body 202 is inserted. Light exits through a distal end 210 of the fiber 208 and illuminates tissue as the endoscope 200 is inserted into a site of an animal including a human. A portion of incident light is reflected back into fiber 208 for subsequence analysis and conversion into an image with a light analyzing and image viewing unit 212. The apparatus 200 also includes a fluid conduit 214 terminating in an exit port 216 near the distal end 206 of the body 202. A proximal end 218 of the fluid conduit 214 is optionally fitted with a Y-connector 220 so that the type of fluid introduced into the fluid conduit 218 can be changed or a fluid, especially a gas, can be introduced to dilate the tissue so that the tissue can be visualized easily.

The apparatus 200 also includes an electrode housing 222 having a proximal end 224 and a distal end 226. Threaded through the housing 222 is a conducting member 228. The conducting member 228 includes an electrode 230 at its distal end 232 and is connected to an electrode extension and retraction unit 234 at its proximal end 236. The electrode extension and retraction unit 234 is adapted to shield the electrode 230 during endoscope 200 insertion and to extend the electrode 230 once the distal end 206 is positioned adjacent a nerve to be stimulated. The extension and retraction unit 234 is connected via a conducting conduit 238 to a nerve stimulator 240 having a second conducting conduit 242 including a second electrode 244 adapted to be placed on the skin to act as ground and to produce a volt difference across the electrodes 230 and 244.

Once the distal end 206 of the endoscope 200 is positioned relying on images or direct views through the fiber 208, the electrode 230 is extended and voltage is applied across the electrode 230 and 244 to stimulate the nerve. If the correct nerve is stimulated evidenced by flex action, then the electrode 230 can be retracted and anesthesia introduced to the site via the fluid conduit 214. The electrodes 230 and 244 and the conducting member can be composed of any conductor and can be of any size. The extension and retraction unit 234 can be a manual device or an electromechanical device that is adapted to push and pull the electrode 230 so that it can be extended or retracted.

Method for Using the Endoscopes of this Invention

Scenario No. 1

Figure 3A:
FIGS. 3A-F depict a method for producing an endoscope insertion site in an animal including a human: (A) depicts a catheter with the insertion needle; (B) depicts the removal of the needle and the insertion of a guide wire into and through the catheter; (C) depicts a dilator threaded down the guide wire to expand a tissue at the insertion site; (D) depicts a trocar including a balloon threaded down the guide wire onto the dilator to further expand the tissue; (E) depicts the trocar in place after removal of the dilator and guide wire and balloon inflation, and (F) depicts the removal of the guide wire and dilator and insertion of an endoscope of this invention.
Figure 3B:
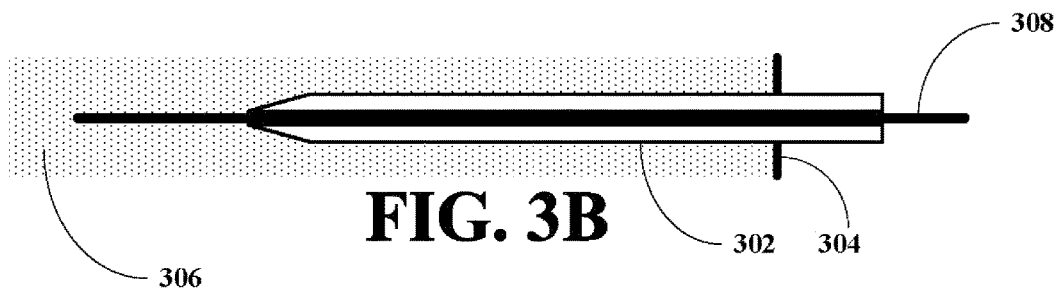
Figure 3C:
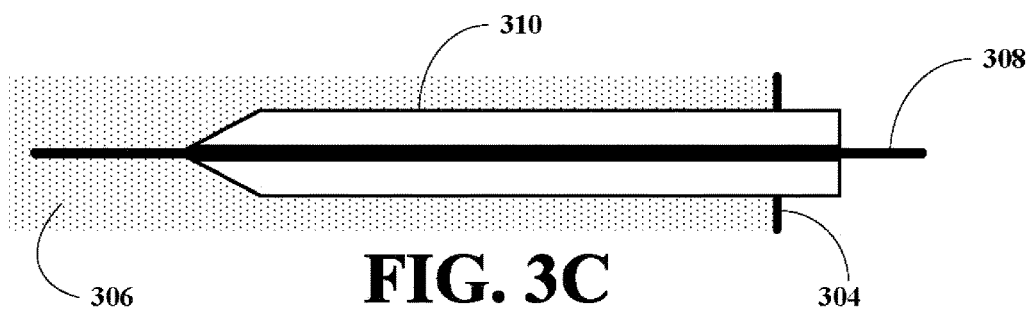
Figure 3D:
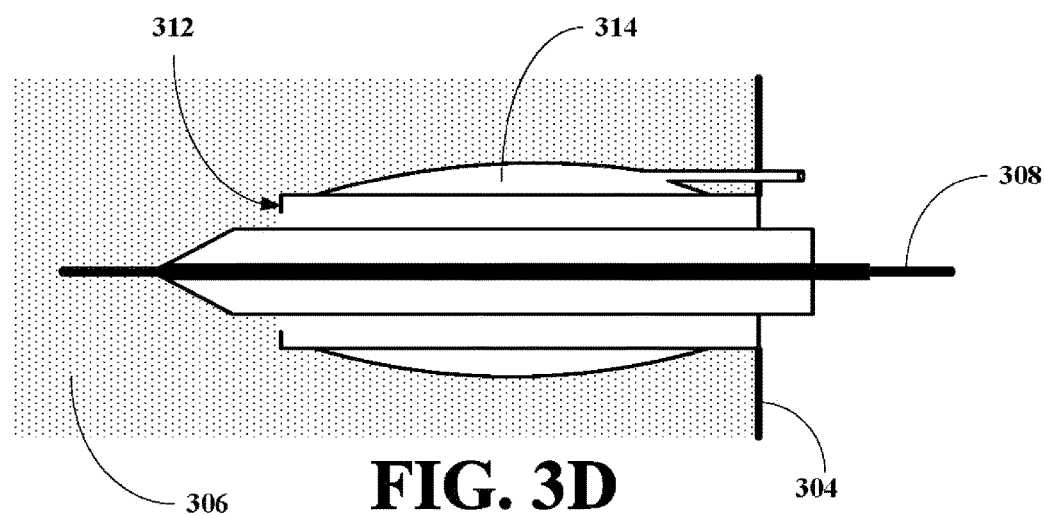
Figure 3E:
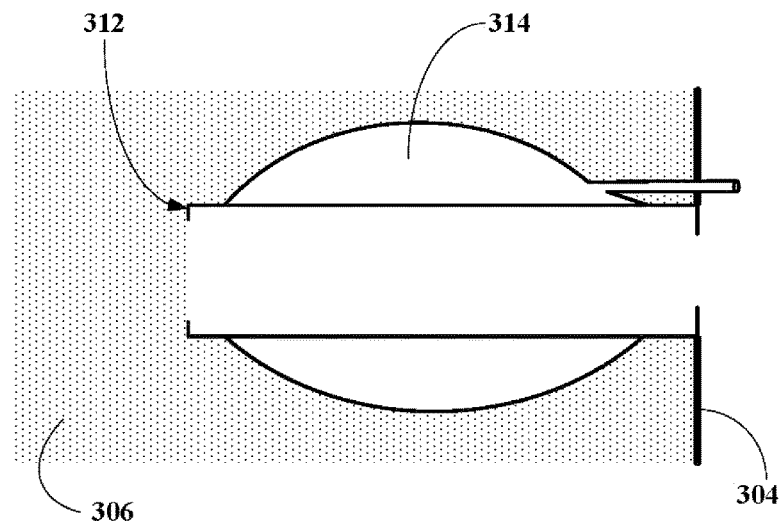
Figure 3F:
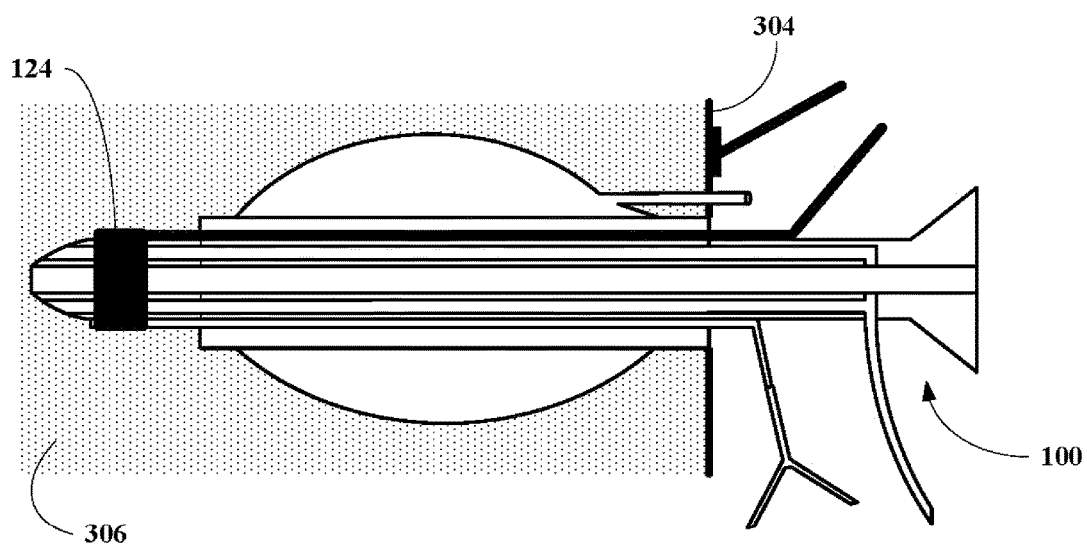

Referring now to FIGS. 3A-F, an embodiment of the method of this invention is shown. Looking at FIG. 3A, the method includes the step of inserting a needle 300 carrying a catheter 302 such as an angiocath through a skin 304 at a tissue site 306 of an animal including a human. Once properly placed, the needle 300 in removed and a guide wire 308 is threaded through the catheter 302 as shown in FIG. 3B. Next, the catheter 302 is removed and a dilator 310 is placed over the wire 308 and pushed into the site 306 to distend the tissue as shown in FIG. 3C. After distending the tissue using the dilator 310, a trocar 312 having a balloon 314 is placed over the dilator 310 and pushed into place to further distend the tissue as shown in FIG. 3D. The guide wire 308 and dilator 310 are then removed leaving the trocar 312 behind and the balloon 314 is inflated to further distend the tissue as shown in FIG. 3E. Next, an endoscope or a fiberoscope of this invention 100 including a ring electrode 124 is inserted through the trocar 312 to provide the ability of directly or through a monitor to visualize the structures and to permit proper positioning of the electrode on the endoscope as shown in FIG. 3F.

Scenario No. 2

Figure 4A:
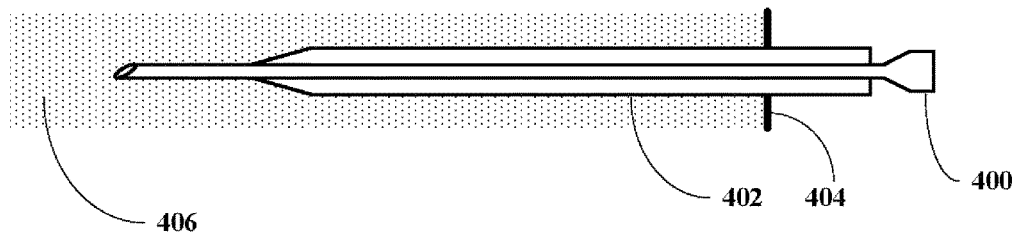
FIGS. 4A-E depict method for producing an endoscope insertion site in an animal including a human: (A) depicts a catheter with the insertion needle; (B) depicts the removal of the needle and the insertion of a guide wire into and through the catheter; (C) depicts a dilator threaded down the guide wire to expand a tissue at the insertion site; (D) depicts removal of the guide wire and insertion of a trocar including a gas conduit for pressure tissue dissection; and (E) depicts the trocar in place and the replacement of the dilator and guide wire with an endoscope of this invention.
Figure 4B:
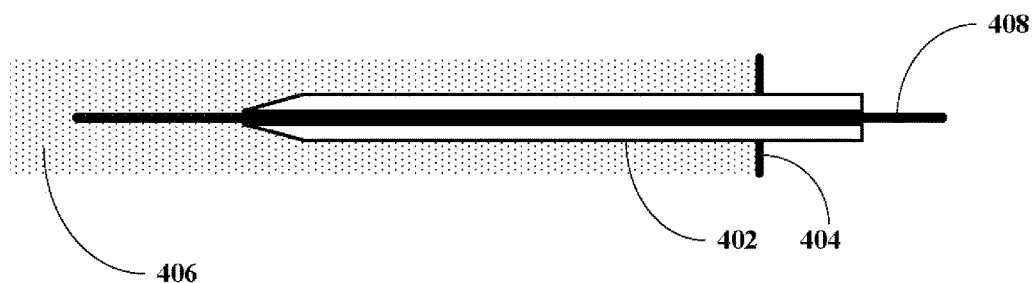
Figure 4C:
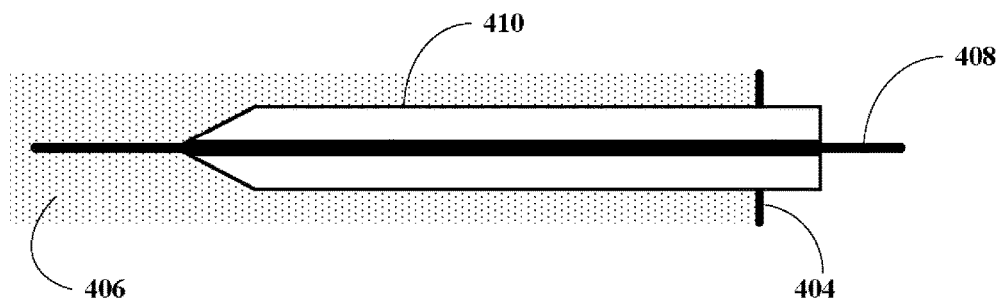
Figure 4D:
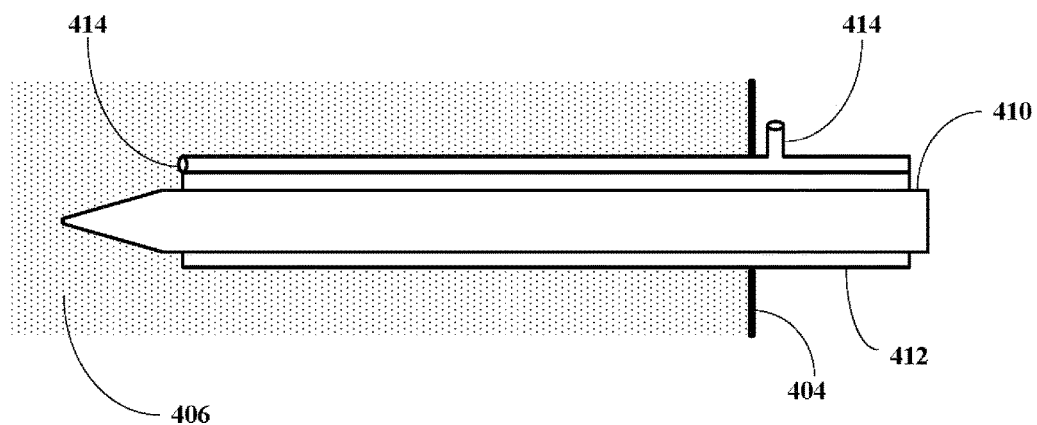
Figure 4E:
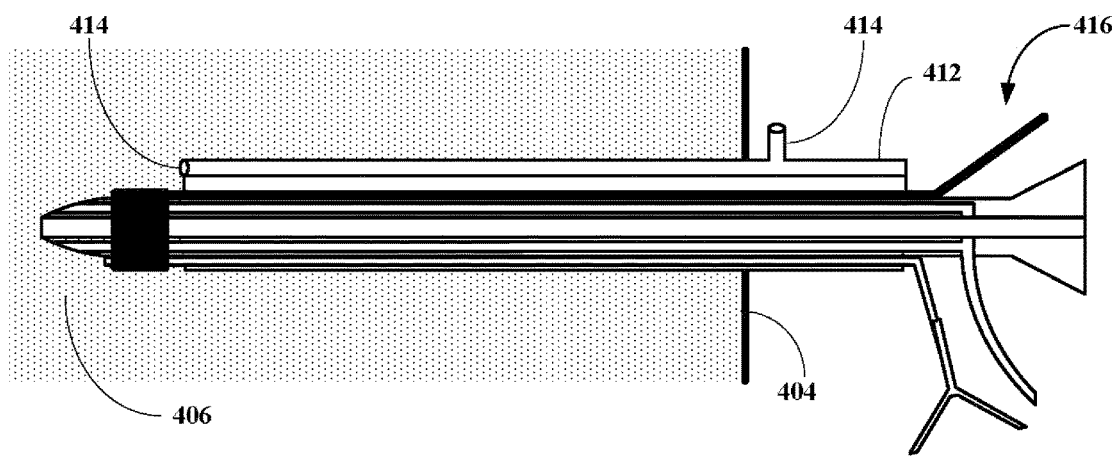

Referring now to FIGS. 4A-e, an embodiment of the method of this invention is shown. Looking at FIG. 4A, the method includes the step of inserting a needle 400 carrying a catheter 402 such as an angiocath through a skin at a site 404 of a tissue 406 of an animal including an human. Once properly placed, the needle 400 in removed and a guide wire 408 is threaded through the catheter 402 as shown in FIG. 4B. Next, the catheter 402 is removed and a dilator 410 is placed over the wire 408 and pushed into the tissue 406 to distend the tissue as shown in FIG. 4C. After distending the tissue using the dilator 410, a trocar 412 having a side port 414 is placed over the guide wire 408 and pushed into place as shown in FIG. 4D. Carbon dioxide is then insufflated at a pressure between about 4 and about 8 mm Hg through the side port 414 to distend the tissue. Next, the dilator 410 is removed and an endoscope or a fiberoscope of this invention 416 is inserted through the trocar 412 to visualize the structures and to permit proper positioning of the electrode on the endoscope as shown in FIG. 4E.

Scenario No. 3

Figure 5A:
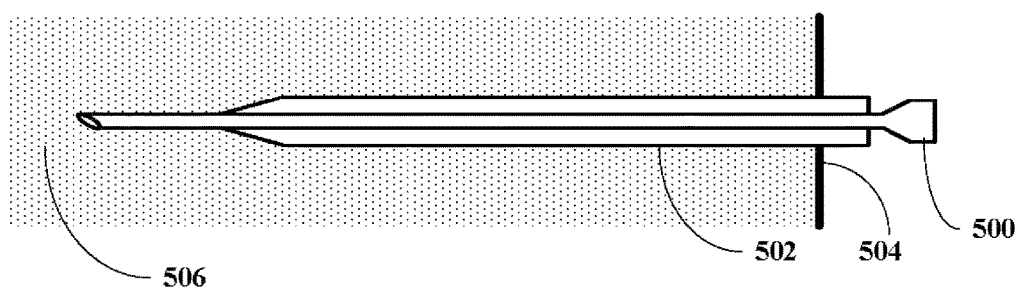
FIGS. 5A-E depict a method for inserting an endoscope into an insertion site of an animal: (A) depicts a catheter with the insertion needle; (B) depicts the removal of the needle and the insertion of a guide wire into and through the catheter; (C) depicts a dilator threaded down the guide wire to expand a tissue at the insertion site; (D) depicts a trocar including a distal balloon and gas tissue expansion conduit threaded down the guide wire replacing the dilator to further expand the tissue; and (E) depicts the replacement of a portion of the trocar with an endoscope of this invention.
Figure 5B:
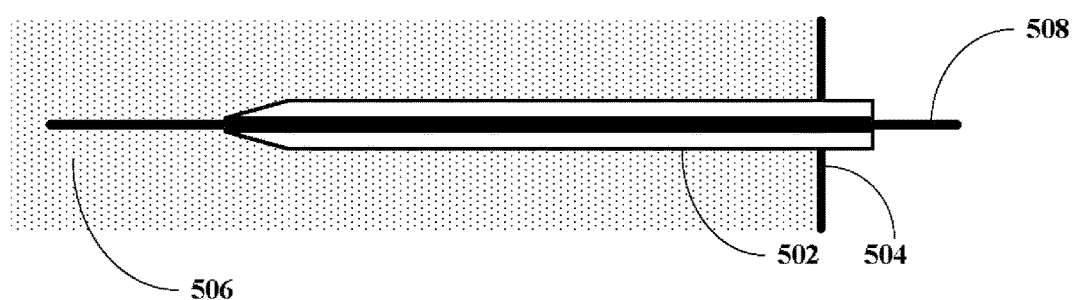
Figure 5C:
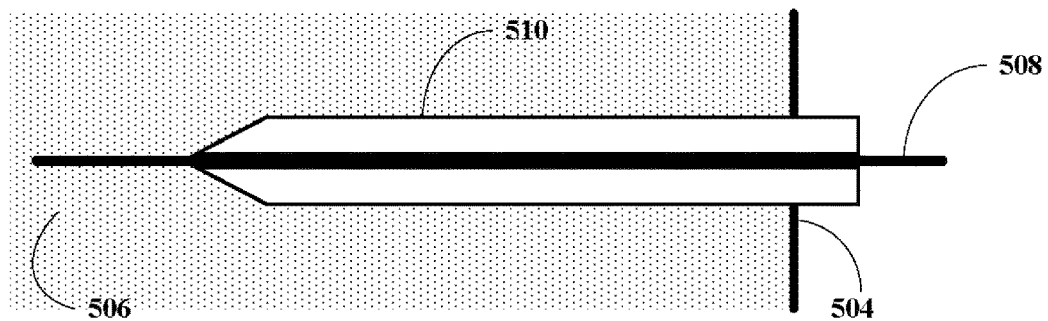
Figure 5D:
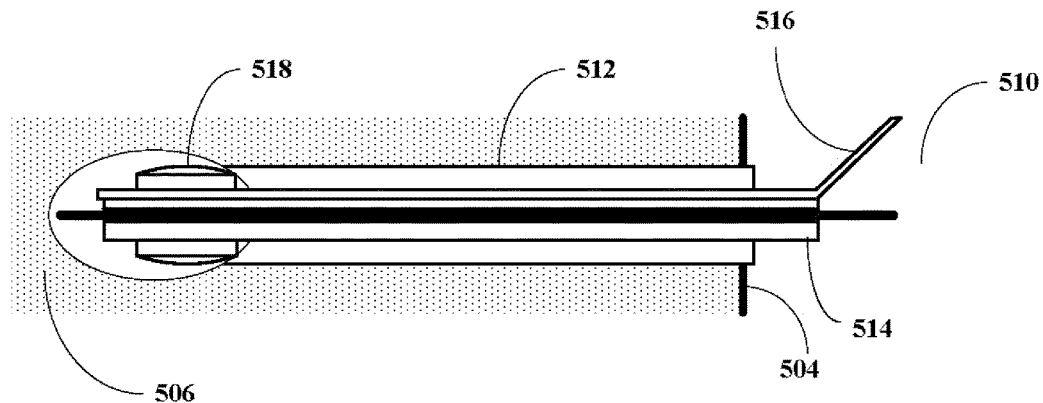
Figure 5E:
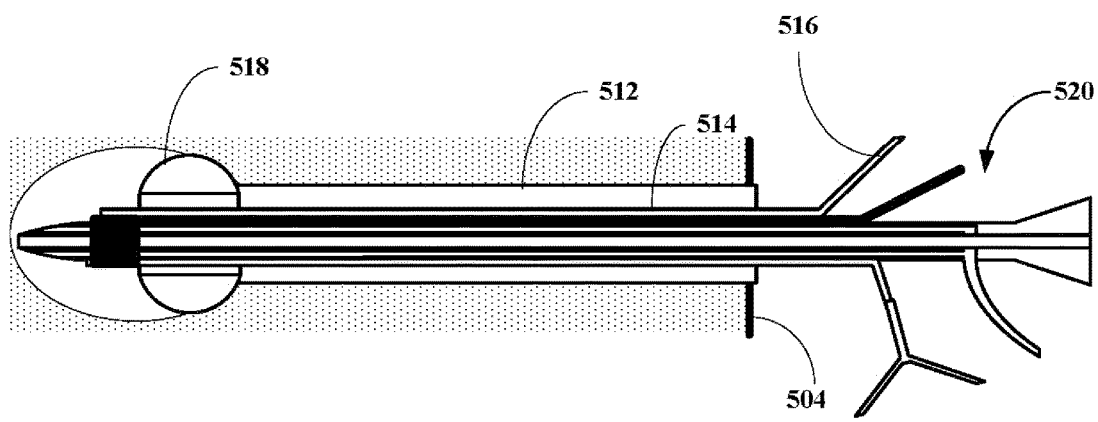

Referring now to FIGS. 5A-E, an embodiment of the method of this invention is shown. Looking at FIG. 5A, the method includes the step of inserting a needle 500 carrying a catheter 502 such as an angiocath through a skin at a tissue site 504 of a tissue 506 of an animal including an human. Once properly placed, the needle 500 in removed and a guide wire 508 is threaded through the catheter 502 as shown in FIG. 5B. Next, the catheter 502 is removed and a dilator 510 is placed over the wire 508 and pushed into the tissue 506 to distend the tissue as shown in FIG. 5C. After distending the tissue using the dilator 510, an introducer 512 is passed over the wire 508, and then a trocar 514 having a side port 516 and a circular balloon 518 is introduced over the introducer 512 into the tissue 506 and insufflate carbon dioxide through the side port 514 using a pressure between about 4 and about 8 mm Hg pressure to create an optical cavity. The balloon 518 is then inflated to further distend the tissue 506. Next, the wire 508 is then removed and a flexible endoscope of this invention 520 is passed through the trocar 514 and introducer 512 to visualize the structures and to permit proper positioning of the electrode on the endoscope as shown in FIG. 5E.

Figure 6:
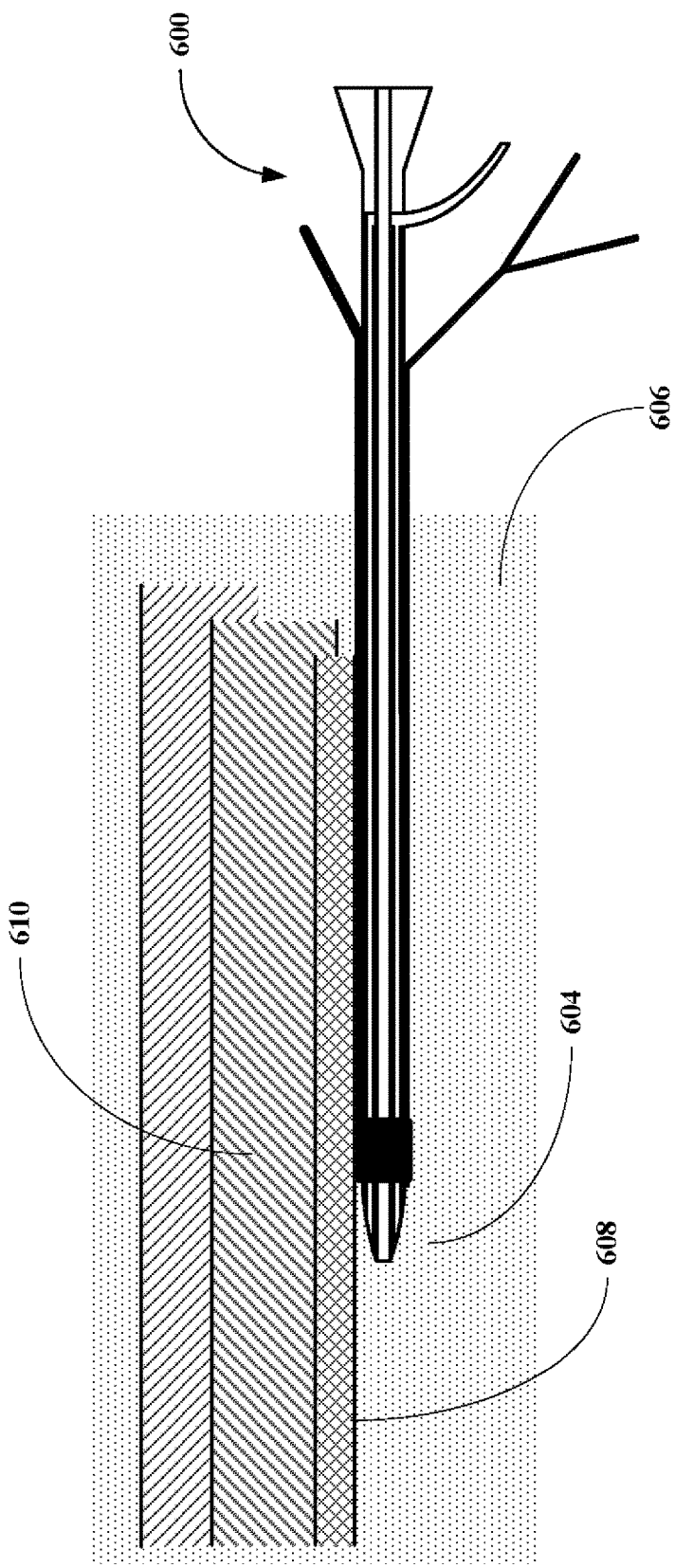
FIG. 6 depict an embodiment of an endoscope of this invention including a distally disposed electrode placed proximal to a nerve to be blocked, where placement adjacent to the nerve is verified by electrode stimulation.

Referring now to FIG. 6, an embodiment of the apparatus, generally 600, is shown positioned adjacent a site 602 of a peripheral nerve 604. The apparatus 600 is located in a tissue 606 showing an artery 608 and a vein 610 traveling near the nerve 604.

First Endoscope Sheath Embodiment

Referring now to FIGS. 7A&B, an embodiment of an endoscope sheath apparatus of this invention, generally 700, is shown to include an endoscope 702 and a sheath 704. The endoscope includes a distal end 706, a proximal or viewing end 708 and a stem 710 therebetween. The sheath 704 is designed to cover at least 50% of a length l of a stem 710 of the endoscope 702. The sheath 704 has a proximal end 712, a distal end 714 and a conduit 716 extending from the distal end 714 and out past the proximal end 712. The conduit 716 ends in a port 718. The endoscope 702 is inserted through the sheath 704 so that a distal portion 720 of the endoscope 702 extending out past the distal end 714 of the sheath 704. The apparatus 700 also includes a stimulating assembly 722. The stimulating assembly 722 includes a stimulating unit 724, a first lead or conducting member 726, an attachment member 728, a second lead or conducting member 730 and a second electrode 732. In certain embodiments, the second electrode 732 is disposed in a skin patch 734 that can be placed on the skin of the animal, including a human, over the distal end 706 of the endoscope 702. The attachment member 728 is detactably connected to the proximal end 708 of the endoscope 702. Because the sheath 704 is constructed out of an insulating material, the portion 720 of the distal end 706 acts as a first electrode when the first and second leads 726 and 730 are connected to the stimulating unit 724. A proximal end 736 of the conduit 716 is optionally fitted with a Y-connector 738 so that the type of fluid or object introduced into the conduit 716 can be changed. For example, a fluid, especially a gas, can be introduced to dilate the tissue so that the tissue can be visualized more easily. The attachment member 728 can be an alligator clip or any device that can form an electric connection between the stimulating unit 724 and the endoscope 702.

For further details on the type of endoscopes that can be equipped with an electrode new block stimulator of this invention include at least the endoscopes disclosed in U.S. Pat. Nos. 7,150,752, 7,134,993, 6,793,622, 6,702,737, 6,699,183, 6,673,060, 6,641,528, 6,595,982, 6,522,933, 6,491,627, 6,482,148, 6,398,776, 6,236,876, 6,203,494, 6,030,360, 6,013,024, 5,960,145, 5,938,588, 5,916,147, 5,752,912, 5,681,263, 5,667,476, 5,575,755, 5,531,664, 5,512,035, 5,464,007, 5,448,989, 5,415,158, 5,396,880, 5,386,816, 5,381,782, 5,359,994, 5,347,989, 5,325,845, 5,301,656, 5,299,559, 5,176,126, 5,167,221, 5,005,558, 4,996,974, 4,967,732, 4,947,827, 4,941,454, 4,834,069, 4,796,607, 4,790,294, 4,787,369, 4,773,395, 4,762,119, 4,762,118, 4,750,477, 4,700,693, 4,688,555, 4,557,254, 4,499,895, 4,483,326, 4,432,349, 4,351,323, 4,294,233, and 4,203,430, incorporated herein by reference.

Second Endoscope Sheath Embodiment

Referring now to FIGS. 8A&B, another embodiment of an endoscope sheath apparatus of this invention, generally 800, is shown to include an endoscope 802 and a sheath 804. The endoscope includes a distal end 806, a proximal or viewing end 808 and a stem 810 therebetween. The sheath 804 has an opened proximal end 812, a closed distal end 814 having a transparent window 816 and a conduit 818 extending from the distal end 814 and out past the proximal end 812. The conduit 816 ends in a port 820. The endoscope 802 is inserted into the sheath 804 through its opened end 812 so that the distal end 806 of the endoscope 802 is in contact with or near the window 816, where near means that the distal end 806 of the endoscope 802 is within 5 mm or less of the window 816. The apparatus 800 also includes a stimulating assembly 822. The stimulating assembly 822 includes a stimulating unit 824, a first lead or conducting member 826, a first electrode 828, a second lead or conducting member 830 and a second electrode 832. In certain embodiments, the second electrode 832 is disposed in a skin patch 834 that can be placed on the skin of the animal, including a human, over the distal end 806 of the endoscope 802. The first electrode 828 is disposed near the distal end 814 of the sheath 804, with the first lead 826 extending through the sheath 804. A proximal end 836 of the conduit 818 is optionally fitted with a Y-connector 838 so that the type of fluid or object introduced into the conduit 818 can be changed. For example, a fluid, especially a gas, can be introduced to dilate the tissue so that the tissue can be visualized more easily.

Needle Endoscopes

Figure 9B:
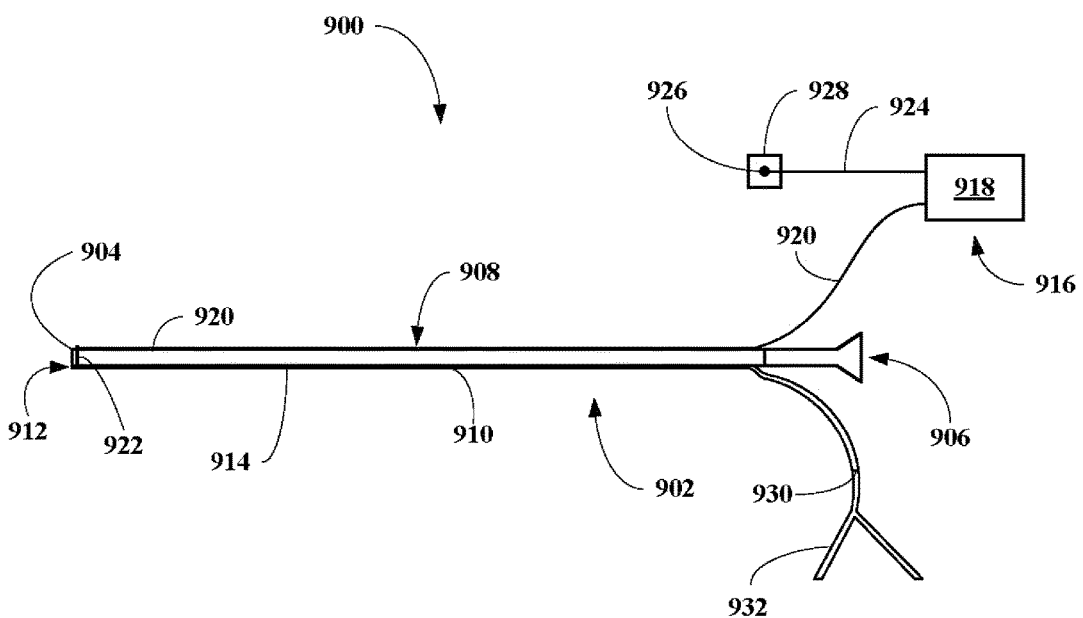

Referring now to FIGS. 9A&B, an embodiment of an endoscope sheath apparatus of this invention, generally 900, is shown to include a needle endoscope 902 having a distal end 904, a proximal or viewing end 906 and a stem 908 therebetween. The endoscope 902 includes a conduit 910 ends in a port 912 extending either through the endoscope 902 (FIG. 9A) or affixed to an outer surface 914 of the endoscope 902 (FIG. 9B). The apparatus 900 also includes a stimulating assembly 916. The stimulating assembly 916 includes a stimulating unit 918, a first lead or conducting member 920, a first electrode 922, a second lead or conducting member 924 and a second electrode 926. In certain embodiments, the second electrode 926 is disposed in a skin patch 928 that can be placed on the skin of the animal, including a human, over the distal end 904 of the endoscope 902. The first electrode 922 is disposed at or near the distal end 904 of the endoscope 902, where the first lead 920 either extends through the endoscope 902 (FIG. 9A) or is affixed to the outer surface 914 of the endoscope 902 (FIG. 9B). A proximal end 930 of the conduit 910 is optionally fitted with a Y-connector 932 so that the type of fluid or object introduced into the conduit 910 can be changed. For example, a fluid, especially a gas, can be introduced to dilate the tissue so that the tissue can be visualized more easily.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

What is claimed is:

1. An integrated and reversibly stimulating anesthetizing endoscope apparatus for peripheral nerve blocks under direct visual control, said endoscopic apparatus comprising:
    an endoscope including a proximal end, a stem section and a distal end;
    a sheath including a proximal end and a distal end, where the sheath surrounds at least 50% of a length of the endo scope stem section and forms a channel between an exterior surface of the endoscope and an interior surface of the sheath,
    a light delivery assembly including at least one light delivery conduit, where each light delivery conduit is connected to a light source and terminates in the distal end of the endoscope, and at least one light receiving conduit, where each light receiving conduit is connected to an image processing and display unit and terminates in the distal end of the endoscope;
    a fluid delivery assembly connected to the sheath, wherein the fluid delivery assembly comprises at least one local anesthetic agent for delivery through the sheath; and
    a nerve stimulating assembly comprising:
        a nerve stimulating unit,
        a first stimulating electrode disposed at or near the distal end of an outside surface of the endoscope and movably associated with the endoscope, wherein the first stimulating electrode is separate from the sheath and disposed in the channel between the exterior surface of the endoscope and the interior surface of the sheath, and wherein the first stimulating electrode is connected via a first conducting member to the nerve stimulating unit, and
        a second electrode adapted to be placed on the skin of a patient and connected via a second conducting conduit to the nerve stimulating unit, where the stimulating unit is adapted to produce a voltage across the first and second electrodes to produce a current that stimulates a nerve response when the first stimulating electrode is proximal a nerve, and wherein the endoscope apparatus is adapted for percutaneous insertion into a tissue site without surgical incision.

2. The apparatus of claim 1, wherein the first stimulating electrode surrounds a portion of the endoscope near its distal end.

3. The apparatus of claim 1, wherein the first stimulating electrode comprises a ring.

4. The apparatus of claim 3, wherein the ring is a solid ring or a wire mesh ring.

5. The apparatus of claim 1, wherein the first stimulating electrode is an exposed distal tip of the endoscope apparatus.

6. The apparatus of claim 1, wherein the first electrode comprises a plurality of electrode elements.

7. The apparatus of claim 1, wherein the first electrode comprises a plurality of electrode elements equally spaced around an outside surface of the endoscope near the distal end of the endoscope.

8. The apparatus of claim 1, further comprising a catheter.

9. The apparatus of claim 1, wherein the fluid delivery assembly includes a Y-connector.

10. The apparatus of claim 1, wherein the light delivery and receiving conduits comprise optical fibers or optical fiber bundles.

11. The apparatus of claim 1, wherein the sheath further comprises a conduit.

12. The apparatus of claim 11, wherein the conduit is within the sheath.

13. The apparatus of claim 11, wherein the conduit is connected to the fluid delivery assembly.

14. The apparatus of claim 11, wherein the conduit has an exit port at the distal end of the sheath, and wherein the conduit extends out past the proximal end of the sheath.

15. The apparatus of claim 1, wherein the first stimulating electrode is retractably disposed along the outside surface of the endoscope.

16. The apparatus of claim 1, wherein the first stimulating electrode is disposed at the distal end of an outside surface of the endoscope.

17. The apparatus of claim 1, wherein the first stimulating electrode is in a field of view of the image processing and display unit.

18. The apparatus of claim 1, wherein the endoscope has a diameter between about 16-gauge needles and about 18-gauge needles.

19. The apparatus of claim 1, wherein the endoscope has a diameter between about 0.5 mm and about 1 mm.

* * * * *